（12） United States Patent
Janssens et al.

(10) Patent No.: US 7,078,578 B2
(45) Date of Patent: Jul. 18, 2006

(54) PROCESS FOR CONVERSION OF OXYGENATES TO HYDROCARBONS AND COMPOSITION FOR USE THEREIN

(75) Inventors: Ton V. W. Janssens, Bagsværd (DK); Søren Dahl, Hillerød (DK); Claus Hviid Christensen, Lynge (DK)

(73) Assignee: Haldor Topsoe A/S, Lyngby (DK)

( * ) Notice: Subject to any disclaimer, the term of this patent is extended or adjusted under 35 U.S.C. 154(b) by 24 days.

(21) Appl. No.: 10/840,651

(22) Filed: May 7, 2004

(65) Prior Publication Data
US 2004/0254409 A1 Dec. 16, 2004

(30) Foreign Application Priority Data
May 17, 2003 (DK) ............................... 2003 00745

(51) Int. Cl.
*C07C 1/02* (2006.01)

(52) U.S. Cl. ..................... 585/640; 585/638; 585/639

(58) Field of Classification Search ............... 585/638, 585/639, 640
See application file for complete search history.

(56) References Cited

U.S. PATENT DOCUMENTS

| 3,894,104 | A | 7/1975 | Chang et al. |
| 4,481,305 | A | 11/1984 | Jorn et al. |
| 4,499,327 | A | 2/1985 | Kaiser |
| 4,520,216 | A | 5/1985 | Skov et al. |
| 5,534,239 | A | 7/1996 | Des Courieres et al. |
| 6,518,475 | B1 | 2/2003 | Fung et al. |
| 6,565,826 | B1 * | 5/2003 | Jacobsen et al. ............. 423/716 |
| 2001/0003117 | A1 * | 6/2001 | Jacobsen et al. .............. 502/69 |
| 2002/0034471 | A1 * | 3/2002 | Jacobsen et al. ............. 423/700 |
| 2002/0038057 | A1 * | 3/2002 | Schmidt et al. ............. 568/385 |
| 2002/0038775 | A1 | 4/2002 | Sterte et al. |
| 2004/0110630 | A1 * | 6/2004 | Schmidt et al. ............... 502/60 |

FOREIGN PATENT DOCUMENTS
WO    WO 01/49607    7/2001

* cited by examiner

*Primary Examiner*—Elizabeth D. Wood
(74) *Attorney, Agent, or Firm*—Dickstein Shapiro Morin & Oshinsky LLP

(57) ABSTRACT

A process for the conversion of oxygenates to hydrocarbons comprising contacting a feed stream comprising oxygenates with a catalyst containing a microporous material under oxygenate conversion conditions, wherein the catalyst contains a crystalline microporous material with intra-crystalline mesopores. The invention also includes a composition for use in the above process.

9 Claims, 4 Drawing Sheets

PROCESS FOR CONVERSION OF OXYGENATES TO HYDROCARBONS AND COMPOSITION FOR USE THEREIN

The present invention is related to a process for the conversion of oxygenates to hydrocarbons. In particular, the process relates to oxygenate conversion using catalysts based on microporous materials.

BACKGROUND OF THE INVENTION

Deactivation by coke formation is a serious problem in many industrial processes in which organic molecules are converted over catalysts based on microporous materials such as zeolites, aluminophosphates (AlPO) or silica-aluminophosphates (SAPO). Examples of such processes are cracking of hydrocarbons, alkylation of hydrocarbons and conversion of oxygenates to hydrocarbons. The existing techniques for reducing this kind of deactivation all affect the catalytic properties of the microporous materials.

To improve properties, such as product yield, selectivity, activity or stability, the microporous materials are often modified by catalytically active materials, promoters or stabilisers when applied as catalysts. Examples are the addition of Ni, W, Pd to a Y-zeolite in a hydrocracking catalyst, or the addition of Ni to a SAPO in the conversion of methanol to ethylene and propylene.

Well known oxygenate conversion processes that make use of catalysts based on microporous materials are Methanol-to-Olefins (MTO) and Methanol-to-Gasoline (MTG). In these processes, methanol is converted to hydrocarbon molecules. In the MTO process, described in U.S. Pat. No. 4,499,327, the desired products are olefins such as ethylene, propylene and butylenes. If the process is aimed at the production of propylene, it is sometimes called Methanol-to-Propylene (MTP). The catalysts commonly used in these processes are based on H-ZSM-5 zeolites or SAPO-34. Such a process is described in U.S. Pat. No. 6,518,475. In the MTG process, described in U.S. Pat. No. 3,894,104, methanol is converted to gasoline. A H-ZSM-5 based catalyst is preferred here.

A process related to the methanol conversions described above is TIGAS. This process, which is further described in U.S. Pat. Nos. 4,481,305 and 4,520,216, integrates the synthesis of methanol and DME from synthesis gas with the conversion of methanol and DME to gasoline, thus obtaining a process in which fuel is synthesised directly from synthesis gas.

The economy of the TIGAS, MTG, MTO and MTP processes depends critically on the stability of the zeolite based catalyst that produces the fuel product. Suppression of catalyst deactivation is therefore of crucial importance for these processes.

The deactivation rate depends on the nature of the reactants and the products, the process conditions and the catalyst formulation. A catalyst deactivated by coke formation can often be regenerated by heating it in an oxygen containing gas stream (typically air or diluted air), which burns off the coke, thus restoring the activity of the microporous catalyst. Very often, the deactivation is so fast that the microporous catalysts have to be continuously regenerated in the chemical plant during operation. In these cases, fluidised bed reactors are often preferred, since in these reactors it is a relatively simple process withdrawing a part of the catalyst for regeneration and thereafter reintroducing it in the reactor.

If deactivation is slower, two or more parallel fixed bed reactors can be used. In such a process, one of the reactors is regenerated while the other(s) is/are used for production. An alternative is to temporarily shut down the plant and regenerate the catalysts. In both cases, it has to be decided how often catalyst regeneration must be performed. This interval is the cycle length and it is the duration a catalyst can be operated without a significant loss in feed conversion. In the MTP process described by Rothaemel, M. et al. (ERTC Petrochemical Conference, March 2003, Paris), incorporated herein by reference, this cycle length is approximately 700 hours. Water may be added to the feed to improve process performance.

Regeneration usually leads to a deterioration of catalyst performance because the regeneration frequently is incomplete and may damage the catalyst. Furthermore, deactivation is inevitably connected with carbon loss in the process, which implies a lower product yield. Finally, the need for catalyst regeneration is an important cost factor, as it makes the process less efficient and always requires additional installations requiring considerable investments. For these reasons, it is desirable to suppress catalyst deactivation by coking as much as possible.

A commonly applied strategy to suppress coke formation is changing the process conditions. For example, a hydrocracking catalyst has a much longer lifetime (more than one year) than a FCC catalyst (approximately one minute), due to the presence of hydrogen in the hydrocracking process. In U.S. Pat. No. 4,520,216, it is disclosed that catalyst deactivation in the TIGAS process is reduced by adjusting process parameters.

Another strategy to avoid coke formation is a change of the properties of the catalyst. For example, catalysts based on dealuminated aluminosilicates normally have a longer lifetime in hydrocarbon conversion processes. However, the dealumination significantly affects the catalysts characteristics (activity/selectivity), since both the number and average activity of the active acid sites are reduced. The use of catalysts with a different micropore structure is sometimes a possibility to avoid coke formation, but this approach implies a change in catalytic characteristics as well, and can have major consequences for the process design.

The connection between the catalytic characteristics and deactivation properties is a problem in catalyst and process design, and always results in a compromise between deactivation and catalytic properties.

Therefore, there is a strong need for a process for oxygenate conversion, in which deactivation by coke formation of catalysts based on microporous materials is suppressed without changing other catalytic properties.

SUMMARY OF THE INVENTION

The objective of the invention is to obtain a process for the conversion of oxygenates to hydrocarbons, in which the coke formation is suppressed and the cycle length for the process is significantly extended.

The invention concerns a process for the conversion of oxygenates to hydrocarbons comprising contacting a feed stream comprising oxygenates with a catalyst containing a microporous material under oxygenate conversion conditions, wherein the catalyst contains a crystalline microporous material with intra-crystalline mesopores.

The invention also concerns a composition for use in the oxygenate conversion process and the composition comprises an oxygenate-containing feedstream and a catalyst containing a microporous material wherein the catalyst contains a crystalline microporous material with intra-crystalline mesopores.

In this oxygenate conversion process, the cycle length is significantly extended, while the product composition is approximately the same as in a conventional process using a microporous catalyst.

DETAILED DESCRIPTION OF THE INVENTION

Figure 1:
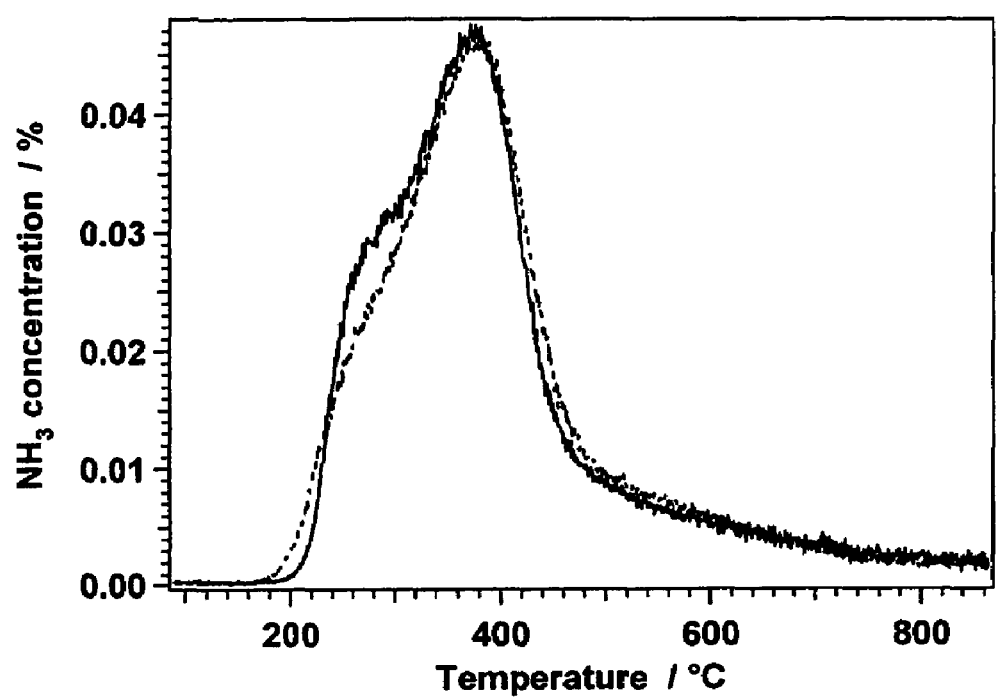
FIG. 1 shows the $NH_3$-TPD profiles of the zeolite catalyst samples used in the methanol-to-gasoline reaction of the first example disclosed in the present application.

As used in the invention the term "microporous materials" comprise materials having a crystalline structure in which pores of molecular dimensions (3–20 Å) exist. These materials include molecular sieves, zeolites, aluminosilicates, silicoaluminophosphates, aluminophosphates and similar materials known to persons skilled in the art.

As used in the invention the term "microporous catalysts" includes any catalyst formulation where the presence of a microporous material is essential for obtaining the desired products.

As used in the invention the term "mesoporous materials" includes any crystalline microporous material, in which intra-crystalline mesopores in the range 2–50 nm have been introduced.

As used in the invention the term "mesoporous catalysts" includes any catalyst formulation as for a microporous catalyst, in which the microporous material is replaced by a mesoporous material.

As used in the invention "feed stream containing oxygenates" includes any process stream containing carbon-containing oxygenates. Examples of such oxygenates can be methanol and dimethyl ether or a combination of these two compounds, though other oxygenates containing carbon, hydrogen and oxygen can be used.

In the process of the invention, a feed stream containing oxygenates is contacted with the catalyst in a reactor under conditions suitable for obtaining the desired product. The feed can be in the form of a gas, a liquid or a combination thereof. The reactor can be a fixed bed reactor, a fluidised bed reactor, a trickle bed reactor or any other type of reactor. The catalyst employed in the process of the invention comprises all mesoporous catalysts according to the definition given earlier.

In the process of the invention, a considerably extended cycle length without a significant loss in production and product yields is achieved by employing a mesoporous catalyst. The mesoporous materials that are used in the mesoporous catalysts can be prepared according to U.S. Pat. Nos. 6,565,826 and 6,620,402, both of which are incorporated herein by reference.

To show the improved performance of the process of the invention, the average hourly conversion of oxygenate per gram catalyst is determined as a function of a relative cycle length for given process conditions. The relative cycle length (RCL) is the ratio of the cycle length in a process and a reference time. The cycle length and thereby the RCL is a process parameter chosen by the operator of the process. Typically, the cycle length in a process converting oxygenates to hydrocarbons is chosen as the time on stream at which the oxygenate conversion has fallen to 95% of its initial value (see for example Rothaemel et al. ERTC Petrochemical Conference, March 2003, Paris). For convenience, the cycle length is defined using a microporous catalyst as the reference time for the given process conditions. This is a useful definition, since the average hourly conversion of oxygenate per gram catalyst starts to decrease at a relative cycle length of one in a process with a microporous catalyst. In the process of the invention, the average hourly conversion of oxygenate per gram catalyst does not start to decrease at a RCL of one but first at a RCL significantly larger than one. This means that in the process of the invention a significantly longer cycle length can be chosen by the operator, without a loss in oxygenate conversion, when compared to a process using a microporous catalyst. This will be further illustrated in the examples.

A commonly used catalyst for the conversion of oxygenates to hydrocarbons is a microporous ZSM-5 zeolite. The catalytic behaviour of microporous zeolites is determined by the crystal structure combined with the amount and strength of the acid sites. By reducing the number and strength of the acid sites in the catalyst, or by changing the process conditions, the period of time in which the catalyst is active in a process for oxygenate conversion can be extended by using a zeolite with less acidic sites. However, this inevitably results in a charge of product composition. A unique feature of a process based on mesoporous zeolite catalysts is that the time interval between catalyst regeneration steps can be considerably extended without significantly affecting the product distribution.

To establish that the mesoporous zeolite and the corresponding microporous zeolite are chemically comparable, both zeolites are characterised by $NH_3$ TPD. In $NH_3$-TPD, the total amount of $NH_3$ that desorbs from the material and the desorption temperature of $NH_3$ are determined simultaneously. This is performed as follows:

A 200 mg sample of the material is heated to 500° C. for 1 hr in an atmosphere of a dry inert gas (e.g. helium or nitrogen). The sample is then cooled down to 150° C. and $NH_3$ is adsorbed by exposing the sample to a mixture of 2% $NH_3$ in an inert gas at the given temperature for 30 minutes, to ensure saturation of the sample with $NH_3$.

After the $NH_3$ adsorption, the sample is purged with dry inert gas for 3 hours at 150° C. and then cooled down to 90° C. Finally, the temperature is raised to 850° C. at a rate of 10° C./min and maintained at this temperature for 15 min. While heating, both the temperature and the concentration of ammonia are recorded, the concentration being determined by a calibrated mass spectrometer. After the experiment, the dry weight of the sample is determined. The total amount of ammonia is found by integration of the measured $NH_3$ concentration versus time profile and multiplying the result by the flow of inert gas. Dividing the total amount of ammonia by the dry weight of the sample yields the acidity expressed as mmol $NH_3$/g dry sample.

The $NH_3$ desorption experiments also contain information on the acid-base chemistry of the materials. A stronger acid site will bind $NH_3$ more strongly. Stronger adsorption results in a higher desorption temperature. Hence, the profile of $NH_3$ concentration as a function of temperature measured in the $NH_3$-TPD experiment described above gives an indication of how much ammonia is adsorbed with a certain adsorption strength, or, in other words, a distribution of the acid strength of the acidic sites in the material. This is used as a fingerprint of the acidic properties of the zeolite sample.

A particular embodiment of the invention is the conversion of a feed containing methanol or dimethyl ether over a mesoporous H-ZSM-5 catalyst to hydrocarbons such as parafins and olefins. The inventive process is illustrated in the examples below by comparison of a microporous H-ZSM-5 catalyst with a mesoporous H-ZSM-5 catalyst at the same reaction conditions. In these examples the two catalysts have similar acidic properties in a methanol-to-gasoline (MTG) reaction and in a methanol-to-olefin (MTO) reaction.

A note on the calculation of the conversion: In the examples below, methanol and DME are treated as one kinetic entity. It is thereby assumed that methanol and DME are in equilibrium at all times. As a consequence, formation of DME is not included in the calculation of the conversion. At 0% conversion, the equilibrium amount of DME may be present, while 100% conversion neither methanol nor DME are present in the reactor outlet stream.

It is emphasised here that neither the catalysts nor the process parameters used in the examples below have been optimised for the process in which they were applied. This is not required, since the definition of the relative cycle length only requires that the microporous and mesoporous catalyst are tested for the same reaction under the same conditions, which are not necessarily the optimal conditions.

The product distribution obtained with a mesoporous and a microporous catalyst are very similar showing that the presence of mesopores only affects the resistance of the catalysts against deactivation. The other properties of both types of catalyst are similar. Therefore, it is expected that introducing mesopores in other types of microporous materials, e.g. alumino-phosphates (AlPO), Silica-Alumina-phosphates (SAPO), Titanium-silicates (TS) result in a similar improved resistance to catalyst deactivation.

The mesoporous catalyst contains crystals of the microporous material with intra-crystallisation mesopores obtained by crystallisation of a microporous material in the presence of a particulate matrix having a predetermined pore structure and particle size, the microporous material having a crystalline structure that contains pores in the range 3–20 Å.

The particulate matrix material is inert and chemically stable under zeolite crystallising conditions. The matrix material can for instance consist of carbon particles and it can be removed from the zeolite crystals by combustion, hydrogenation, selective dissolution, evaporation or a combination of these methods. The microporous material can be modified by ion exchange or deposition or impregnation of catalytically active material or catalyst promoters. It can also be modified by passivation of active centers with inert material. Further details on the preparation of the mesoporous catalyst are given in U.S. patent application No. 2001/0003117 as mentioned earlier.

The oxygenate comprising feed stream can for instance be an alkane, alkene and/or aromate stream. The hydrocarbons obtained by the process of the invention are, amongst others, ethylene, propylene or butylenes or combinations of these. The hydrocarbons can be hydrocarbon mixtures with boiling points in the range of 50–150° C.

To perform a methanol-to-gasoline reaction, a feed of 50 mol % methanol in nitrogen is contacted with 200 mg of a H-ZSM-5 zeolite catalyst in a glass-lined U-tube shaped plug-flow reactor (4 mm inner diameter) at a flow rate of 20 Nml/min (1 Nml corresponds to 1 ml at 1 atm and 0° C.), a pressure of 1 atm and a temperature of 370° C. The reaction is carried out with both a mesoporous H-ZSM-5 zeolite and a conventional microporous H-ZSM-5 zeolite. The zeolites were selected such that the $NH_3$ adsorption capacity and the ammonia desorption profile for both samples were approximately the same to ensure that both samples are equivalent, except for the presence of mesopores in one sample. The $NH_3$-TPD profiles of the samples used are given in FIG. 1 and indicate that the samples are largely equivalent in their ammonia adsorption properties. The $NH_3$ adsorption capacity was 0.20±0.03 mmol/g for both samples.

Figure 2:
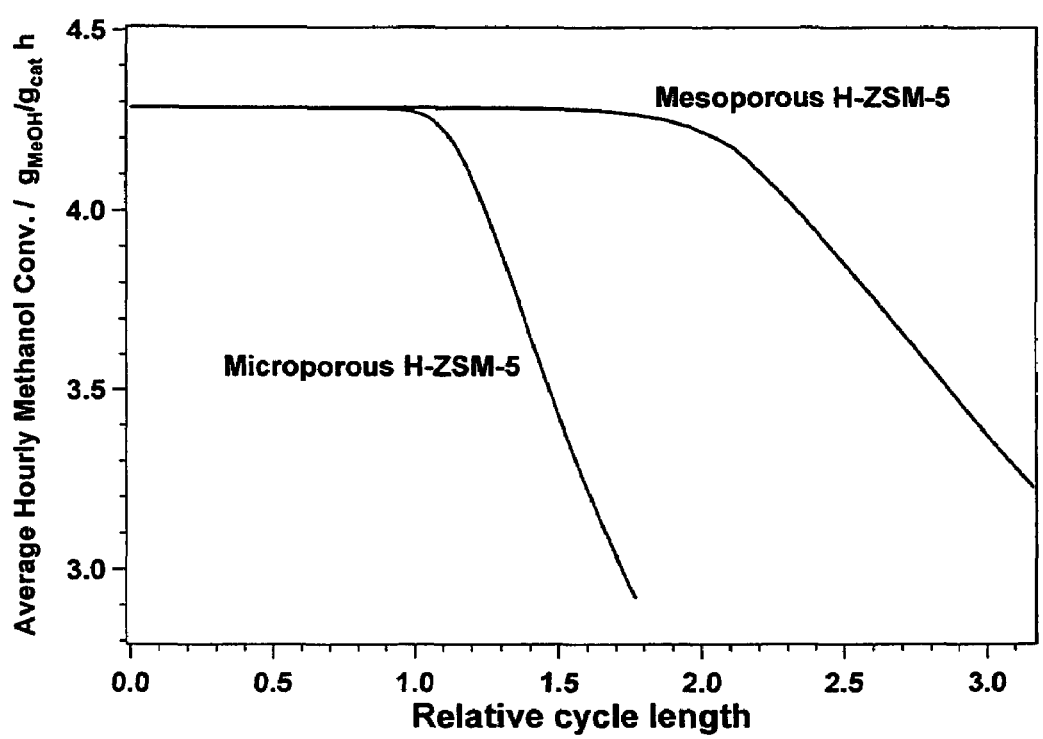
FIG. 2 shows the average hourly methanol conversion as a function of the relative cycle length (RCL) between two regeneration steps in the first example.

FIG. 2 shows the average hourly methanol conversion as a function of the relative cycle length (RCL) between two regeneration steps. The data in FIG. 2 show that the cycle length in a process with the mesoporous catalyst can be extended with a factor of 2 without significant loss in methanol conversion compared to the process with the microporous catalyst.

The products obtained in the MTG reaction are methane, ethylene, ethane, propylene, propane, $C_4$ (isobutane and isobutenes) and $C_{5+}$, which basically is the gasoline fraction. The product distribution at 100% conversion is given in Table 1. It is similar for both the microporous and the mesoporous catalysts indicating that the catalytic properties of microporous H-ZSM5 zeolite are not significantly changed by the introduction of mesopores. The yields listed in Table 1 express the amount of methanol converted to the indicated product.

TABLE 1

Product yield in % obtained using microporous H-ZSM-5 and mesoporous H-ZSM-5.

| Example Process Press/temp | Example 1 MTG 1 bar 370° C. | | Example 2 MTG 6 bars 370° C. | | Example 3 MTO 1 bar 500° C. | |
|---|---|---|---|---|---|---|
| Catalyst | micro-porous | meso-porous | micro-porous | meso-porous | micro-porous | meso-porous |
| Methane | 1.0 | 0.5 | 0.8 | 0.9 | 4.5 | 4.1 |
| Ethylene | 5.8 | 5.3 | 0.5 | 0.3 | 16.6 | 14.8 |
| Propylene | 10.7 | 9.7 | 10.4 | 7.4 | 25.0 | 27.3 |
| Propane | 7.0 | 3.9 | 1.6 | 2.8 | 4.2 | 3.5 |
| C4 | 28.6 | 27.9 | 23.6 | 23.3 | 19.6 | 21.3 |
| C5+ | 46.7 | 52.7 | 61.2 | 63.7 | 29.3 | 28.5 |

EXAMPLE 2

The methanol-to-gasoline reaction is performed with both a microporous catalyst and a mesoporous catalyst identical to those used in Example 1. The feed and process conditions were identical with the exception that the total pressure in the reactor is raised to 6 bar.

Figure 3:
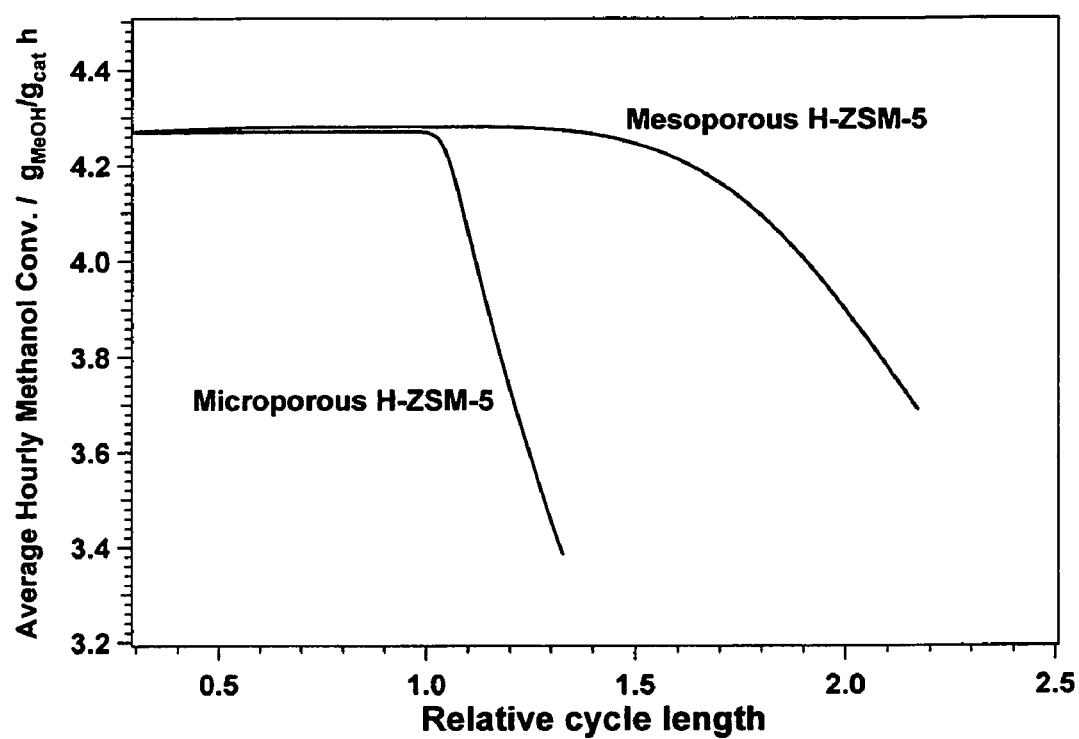
FIG. 3 shows the average hourly methanol conversion as a function of the RCL for the methanol-to-gasoline reaction of Example 2.

The average hourly methanol conversion as a function of the RCL is displayed in FIG. 3. In this example, the cycle length can be extended by a factor of about 1.5 by replacing the microporous catalyst with a mesoporous catalyst.

The product distribution as explained in Example 1 and shown in Table 1 is again similar in both experiments indicating that the chemical nature of both zeolite catalysts is not significantly affected by introduction of the mesopores.

EXAMPLE 3

The methanol-to-olefin reaction is performed with the same U-tube reactor, feed and process conditions as in Example 1 except for the temperature, which is 500° C. in this case. The catalyst samples are identical to the samples used in Example 1.

Figure 4:
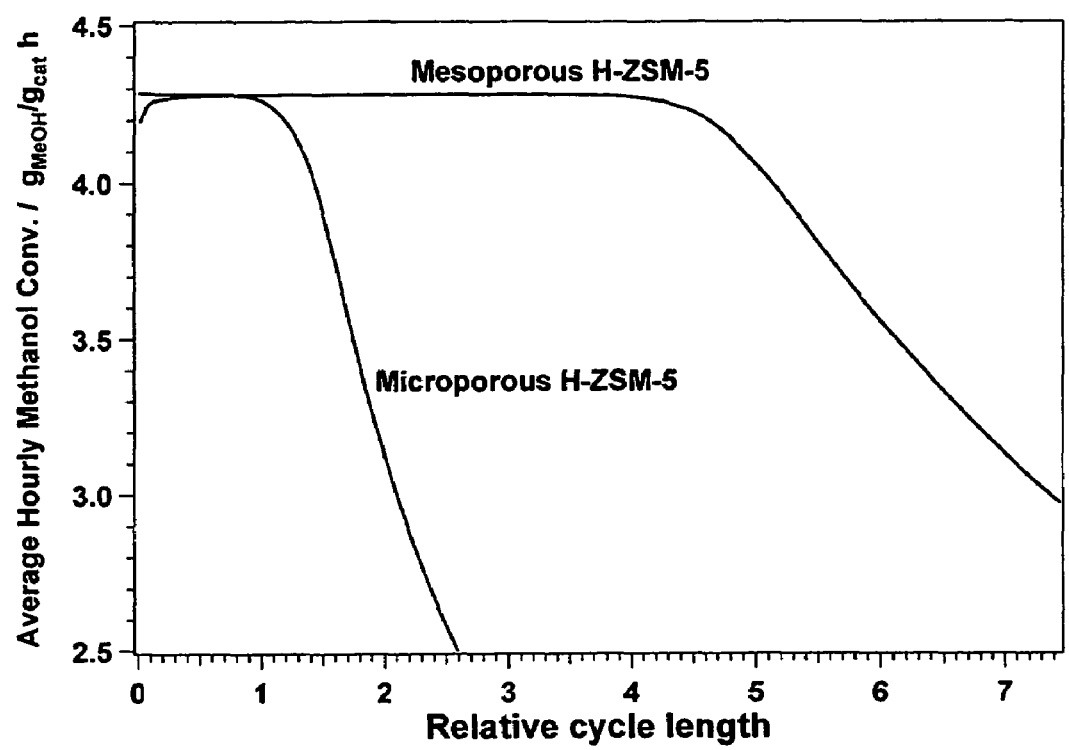
FIG. 4 shows the average hourly methanol conversion as a function of the RCL for the methanol-to-olefin reaction of Example 3.

The average hourly methanol conversion as a function of the RCL for this MTO reaction is displayed in FIG. 4. In this process, the cycle length can be extended by a factor of about 4 without significant loss in methanol conversion by applying the process of the invention.

The products in this reaction are basically the same as mentioned in Examples 1 and 2, but the yield of olefins is higher under these conditions. The product distribution, as shown in Table 1, indicates that the catalytic behaviour of the microporous catalyst and the mesoporous catalyst are very similar and therefore shows that the chemical nature of the zeolite catalysts is not significantly affected by introduction of the mesopores.

The invention claimed is:

1. A process for the conversion of oxygenates to hydrocarbons comprising contacting a feed stream comprising oxygenates with a catalyst containing a microporous material under oxygenate conversion conditions wherein the catalyst contains a crystalline microporous material with intra-crystalline mesopores in the range of 2–50 nm.

2. A process according to claim 1, wherein the ratio of cycle length using the crystalline microporous material with intra-crystalline mesopores to the cycle length using microporous material without intra-crystalline mesopores is larger than 1.

3. A process according to claim 1, wherein the microporous material is a crystalline aluminosilicate, crystalline silico-aluminophosphate, crystalline alumino-phosphate, crystalline titanium silicate or crystalline zeolite.

4. A process according to claim 3, wherein the microporous material is crystalline zeolite.

5. A process according to claim 4, wherein the zeolite is a ZSM-5 zeolite.

6. A process according to claim 1, wherein the oxygenates in the feed stream comprise methanol, dimethyl ether or a combination thereof.

7. A process according to claim 1, wherein the feedstream includes water.

8. A process according to claim 1, wherein the hydrocarbons comprise ethylene, propylene or butylenes or a combination thereof.

9. A process as in claim 1, wherein the hydrocarbons comprise a mixture of hydrocarbons with boiling points in the range of 50–150° C.

* * * * *